US010328085B2

(12) United States Patent
Szade et al.

(10) Patent No.: US 10,328,085 B2
(45) Date of Patent: *Jun. 25, 2019

(54) COBALT PORPHYRINS FOR THE TREATMENT OF BLOOD-RELATED DISORDERS

(71) Applicant: UNIWERSYTET JAGIELLONSKI, Cracow (PL)

(72) Inventors: Agata Szade, Cracow (PL); Krzysztof Szade, Cracow (PL); Alicja Jozkowicz, Cracow (PL); Jozef Dulak, Cracow (PL)

(73) Assignee: UNIWERSYTET JAGIELLONSKI, Cracow (PL)

( * ) Notice: Subject to any disclaimer, the term of this patent is extended or adjusted under 35 U.S.C. 154(b) by 0 days.

This patent is subject to a terminal disclaimer.

(21) Appl. No.: 16/018,229

(22) Filed: Jun. 26, 2018

(65) Prior Publication Data

US 2018/0296569 A1    Oct. 18, 2018

Related U.S. Application Data

(63) Continuation-in-part of application No. 15/309,485, filed as application No. PCT/PL2015/050014 on May 9, 2015, now Pat. No. 10,010,557.

(30) Foreign Application Priority Data

May 9, 2014   (PL) .......................................... 408169

(51) Int. Cl.
*A61K 31/555*    (2006.01)
*A61P 7/00*    (2006.01)

(52) U.S. Cl.
CPC .............. *A61K 31/555* (2013.01); *A61P 7/00* (2018.01)

(58) Field of Classification Search
None
See application file for complete search history.

(56) References Cited

U.S. PATENT DOCUMENTS

| | | | | |
|---|---|---|---|---|
| 4,948,792 | A | 8/1990 | Kappas et al. | 514/185 |
| 5,149,697 | A | 9/1992 | Johnson et al. | 514/185 |
| 5,192,757 | A | 3/1993 | Johnson et al. | 514/185 |
| 5,776,966 | A | 7/1998 | North | 514/410 |
| 2012/0039987 | A1 | 2/2012 | Yuasa et al. | 424/450 |

FOREIGN PATENT DOCUMENTS

| | | | |
|---|---|---|---|
| WO | WO 93/24127 | 12/1993 | ............ A61K 31/40 |
| WO | WO 2011/099602 A1 | 8/2011 | ........... A61K 31/409 |

OTHER PUBLICATIONS

International Search Report dated Jul. 8, 2015 in related application No. PCT/PL2015/050014.
Written Opinion dated Jul. 8, 2015 in related application No. PCT/PL2015/050014.
Polish Search Report dated Jul. 3, 2014 in related application No. P.408169.
Szade et al.: *Murine bone Marrow Lin⁻Sca⁻CD45⁻ Very Small Embryonic-Like (VSEL) Cells Are Heterogeneous Population Lacking Oct-4A Expression*; PLOS One; May 17, 2013.
Mashregfii et al.; *Inhibition of endritic Cell Maturation and Function Is Independent of Henn Oxygenase 1 but Requires the Activation of STAT3*[1]; The Journal of Immunology; Jun. 15, 2008; pp. 7919-7930.
Smith; *Porphyrins and Metalloporphyrins*; Elsevier Scientific Pub. Co (1975) ISBN 0-444-41375-8.
Kenner et al.; *Schutz der Porphyrinvinylgruppen Eine Synthese von Koproporphyrin-III aus Protoporphyrin-IX*: Liebigs Ann. Chem. 1973, 1329-1338; Concise explanation is provided in the English language Abstract.
Burns et al.. *Syntheses of Chlorins from Unsymmetrically Substituted Iron Porphyrins*; J. Chem. Soc., Perkin Trans. 1, 1988, 3119.
Office Action dated Jun. 16, 2017 in related U.S. Appl. No. 15/309,485.
Response to Office Action dated Jun. 16, 2017 as filed Aug. 24, 2017 in related U.S. Appl. No. 15/309,485.
Office Action dated Nov. 24, 2017 in related U.S. Appl. No. 15/309,485.
Response to Office Action dated Nov. 24, 2017 as filed Feb. 23, 2018 in related U.S. Appl. No. 15/309,485.
Advisory Action dated Feb. 28, 2018 in related U.S. Appl. No. 15/309,485.
Notice of Allowance dated Mar. 8, 2018 in related U.S. Appl. No. 15/309,485.

*Primary Examiner* — Heidi Reese
(74) *Attorney, Agent, or Firm* — Renner Kenner Greive Bobak Taylor & Weber (57) ABSTRACT

The use of cobalt porphyrins for the manufacture of an agent for mobilizing bone marrow cells to peripheral blood, preferably used to treat congenital neutropenia, for the treatment and prevention of neutropenia caused by chemotherapy, radiotherapy and pharmacologically-induced neutropenia, for the treatment of acute myeloid leukemia, acute lymphocytic leukemia, myelodysplastic syndromes, and to increase the amount of circulating hematopoietic stem cells in peripheral blood for subsequent isolation in the process of apheresis and allogeneic or autologous transplantation.

7 Claims, 7 Drawing Sheets

COBALT PORPHYRINS FOR THE TREATMENT OF BLOOD-RELATED DISORDERS

CROSS-REFERENCE TO RELATED APPLICATION

This application is a continuation-in-part application of prior application Ser. No. 15/309,485, filed Nov. 8, 2016, which is a § 371 application of International Patent Application No. PCT/PL2015/050014, filed May 9, 2015, which claims benefit of Polish Patent Application No. P.408169, filed on May 9, 2014, all of which are incorporated herein by reference.

TECHNICAL FIELD

The present invention is the use of cobalt porphyrins, particularly cobalt protoporphyrin IX, in the mobilization of peripheral blood cells.

BACKGROUND ART

Peripheral blood cells originate from the hematopoietic stem and progenitor cells (HSPC) residing in the bone marrow. Hematopoietic stem and progenitor cells in the bone marrow repeatedly divide and pass through successive stages of differentiation. Then, the resulting mature and functional cells are released from the bone marrow into the bloodstream.

The process of formation and release of blood cells from the bone marrow into the circulation is strictly regulated by a number of biological factors. It is now known that this process can be regulated pharmacologically—administration of G-CSF (ang. granulocyte colony stimulating factor) results in an enhanced production of granulocyte progenitor cells in the bone marrow and their increased release into the bloodstream. This process is called mobilization and has important clinical implications.

Acute decline in cell numbers in the blood is often observed in patients receiving chemotherapy as anti-tumor therapy. It increases the risk of infections which may have serious consequences and interferes with the anticancer treatment. In this case, administration of G-CSF increases mobilization of cells from bone marrow to the blood and restores the number of white blood cells to normal levels.

Another important use of mobilization by G-CSF is the preparation of a donor during HSPC transplantation. Currently cells isolated from peripheral blood are transplanted for the bone marrow reconstruction. The number of transplanted stem cells is crucial for the success of transplantation. In order to increase the number of stem cells circulating in blood G-CSF is administered to donors prior to the blood collection.

Currently for clinical applications for the mobilization of cells into the bloodstream G-CSF analogs (mainly a drug called filgrastim) are used. These are recombinant proteins produced in *E. coli*. The production of such proteins is complicated and expensive. In addition, G-CSF analogs prepared by this technique are not glycosylated, as are proteins naturally occurring in humans.

Porphyrins are a group of heterocyclic organic compounds consisting of four pyrrole rings connected by methine bridges. In terms of structure, all compounds of this group are derived from the simplest porphyrin called porphine. Synthetic porphyrins are widely used as ligands in the complex compounds used for catalysis. Currently, related compounds are used in medicine: porphyrins in photodynamic therapy and heme arginate in the treatment of acute hepatic porphyria. In clinical trials, tin protoporphyrin was used in the treatment of neonatal jaundice. Use of a porphyrin in photodynamic therapy is disclosed for example in U.S. Pat. No. 5,776,966 and International Application Publication No. WO9324127, which describe a method for selectively reducing the level of active leukocytes in blood or bone marrow, by administering a green porphyrin, and then subjecting the blood or bone marrow to radiation absorbed by those porphyrins. This therapy is designed especially for people suffering from autoimmune diseases and patients infected with HIV. Metal protoporphyrins, including cobalt protoporphyrin, are disclosed in U.S. patent application Publication No. US2012/0039987 for protecting living bodies from disorders such as inflammation, nervous system diseases, atherosclerosis and diabetes which are related to or brought about by an increase in reactive oxygen species. Cobalt porphyrins have also been proposed for use in the treatment of obesity (see U.S. Pat. Nos. 5,149,697 and 5,192,757). Porphyrins have not yet been combined with the process of mobilization of cells, or for treatment of autoimmune diseases directly.

SUMMARY OF THE INVENTION

The core of the invention is the use of cobalt porphyrins for the manufacture of an agent for mobilizing bone marrow cells to peripheral blood. Such agent could preferably be used in the treatment of congenital neutropenias (genetic, autoimmune and idiopathic), in the treatment and prevention of neutropenia caused by chemotherapy, radiotherapy and pharmacologically-induced, in the treatment of acute myeloid leukemia, acute lymphocytic leukemia, myelodysplastic syndromes, and to increase the amount of circulating hematopoietic stem cells in peripheral blood for subsequent isolation in the process of apheresis for allogeneic or autologous transplantation.

Preferably as cobalt porphyrin the cobalt protoporphyrin IX (CoPP) can be used.

Cobalt porphyrin may be administered to patients subcutaneously or intramuscularly. The length of the administration period and cobalt porphyrin dose depends on the observed therapeutic effect (the level of neutrophils or the amount of circulating stem cells in the blood of a patient or a cell donor). In the case of congenital neutropenia, cobalt porphyrin administration dosing regimen will be determined by the attending physician based on the clinical condition of the patient and the therapeutic effects observed. Preferably, the cobalt porphyrin can be administered at a dose in the range of 0.5-50 µmol/kg body weight daily for a period of 3-7 days.

Cobalt porphyrins can be prepared by known methods. For example, cobalt protoporphyrin IX can be prepared using methods as described in: "Porphyrins and Metalloporphyrins" Ed. by K. M. Smith, Elsevier Scientific Pub. Co (1975) ISBN 0-444-41375-8 oraz Kenner, G. W., et al., Liebigs Ann. Chem. 1973, 1329-1338 and Burns, D. H., et al., J. Chem. Soc., Perkin Trans. 1, 1988, 3119. Cobalt protoporphyrin is soluble in alkaline aqueous solutions. In the production process and the preparation of a medical agent cobalt protoporphyrin is proposed to be dissolved in an alkaline solution (eg. 0.2 M $Na_3PO_4.12H_2O$; ~0.2 ml/ml final volume) and then with sterile water (~0.7 ml/ml final volume), pH adjusted to 7.5-7.8 (eg. 0.3N HCl).

Administration of a cobalt protoporphyrin increases the level of G-CSF in the blood, resulting in mobilization of leukocytes, particularly granulocytes, into the peripheral blood. This compound is also easier and cheaper in production than recombinant protein. Administration of cobalt protoporphyrin increases the level of G-CSF in the blood, which also is believed to have some anti-inflammatory properties related to modulation of T cell response. Still further, administration of a cobalt protoporphyrin such as cobalt protoporphyrin IX (CoPP) also increases the level of G-CSF which also has immunomodulatory properties. In the case of autoimmune diseases, increasing the level of G-CSF induces or enhances a response in the blood cells to the autoimmune diseases, thereby altering or alleviating the symptoms autoimmune diseases. The autoimmune diseases that would be treated include, but are not necessarily limited to, systemic lupus erythematosus, inflammatory bowel diseases, rheumatoid arthritis, and diabetes.

Accordingly, at least one aspect of the present invention resides in a method for the treatment of at least one disease selected from the group consisting of congenital neutropenia, neutropenia caused by chemotherapy, radiotherapy and pharmacologically-induced neutropenia, acute myeloid leukemia, acute lymphocytic leukemia, and myelodysplastic syndromes, the method comprising inducing mobilization of bone marrow cells to peripheral blood by administering to a patient in need of an increase of G-CSF in the patient's bone marrow or peripheral blood, an effective amount of a solution containing cobalt protoporphyrin IX by intramuscular or subcutaneous injection or oral administration, to increase the available G-CSF in the bone marrow or peripheral blood.

Another aspect of the present invention may reside in a method for increasing the amount of circulating hematopoietic stem cells in peripheral blood for subsequent isolation in a process of apheresis for allogeneic or autologous transplantation, the method comprising inducing mobilization of bone marrow cells to peripheral blood by administering to a patient in need of an increase in G-CSF in the patient's bone marrow or peripheral blood, an effective amount of a solution containing cobalt protoporphyrin IX by intramuscular or subcutaneous injection or oral administration, to increase the available G-CSF in the bone marrow or peripheral blood.

Yet another aspect of the present invention may be directed to a method for the treatment of at least one disease selected from the group consisting of autoimmune diseases, systemic lupus erythematosus, inflammatory bowel diseases, rheumatoid arthritis, and diabetes in which increase in G-CSF concentration in blood is needed, the method comprising inducing modulation of T cell response by G-CSF by administering to a patient in need of an increase in G-CSF in the patient's peripheral blood an effective amount of a solution containing cobalt protoporphyrin IX by intramuscular or subcutaneous injection or oral administration to increase the available G-CSF in the peripheral blood. The step of inducing modulation preferably includes inducing a Th2 response by administering the solution.

In all embodiments, the cobalt protoporphyrin IX is used in a preferred dose range of 0.5-50 µmol/kg of body weight.

BRIEF DESCRIPTION OF THE DRAWINGS

The possibility of using CoPP for cell mobilization has been confirmed in experiments conducted on two different strains of mice: C3H (5 mice per group) and C57BL6xFVB (5-6 mice per group). The figures show.

BEST MODE FOR CARRYING OUT THE INVENTION

Figure 7:
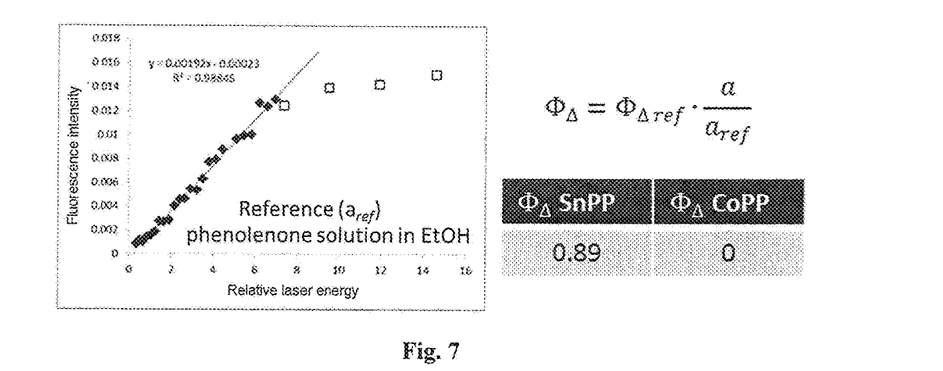

Because of the fact that potential described side effects of administration of porphyrins are associated with photosensitization, causing the formation of toxic reactive oxygen species, it was evaluated if CoPP is a photosensitizer and thus may cause side effects. To this end, the ability to generate reactive oxygen species by CoPP was verified by flash photolysis. It has been shown that, in contrast to many other porphyrins (eg. control SnPP) CoPP does not generate singlet oxygen upon absorption of the laser light at 355 nm. In contrast, in experiment with another porphyrin (SnPP) 89% of absorbed energy was used for generation of singlet oxygen (FIG. 7). It is therefore unlikely that CoPP will cause photosensitization, what often limits the clinical application of other compounds from the group of porphyrins.

Figure 1:
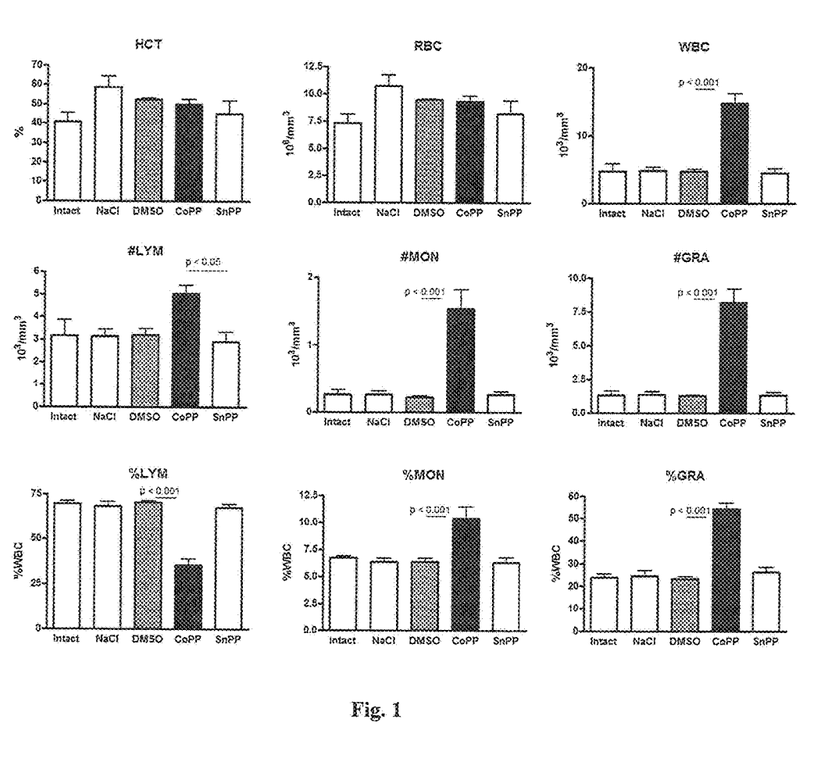
FIG. 1—peripheral blood cell counts in C3H mice after administration of the test compounds (HCT—hematocrit, RBC—erythrocytes, WBC—leukocytes, LYM—lymphocytes, MON—monocytes, GRA—granulocytes, #—number of cells per $mm^3$, %—percentage of the population among all leukocytes; (ANOVA+Bonferroni test)
Figure 3:
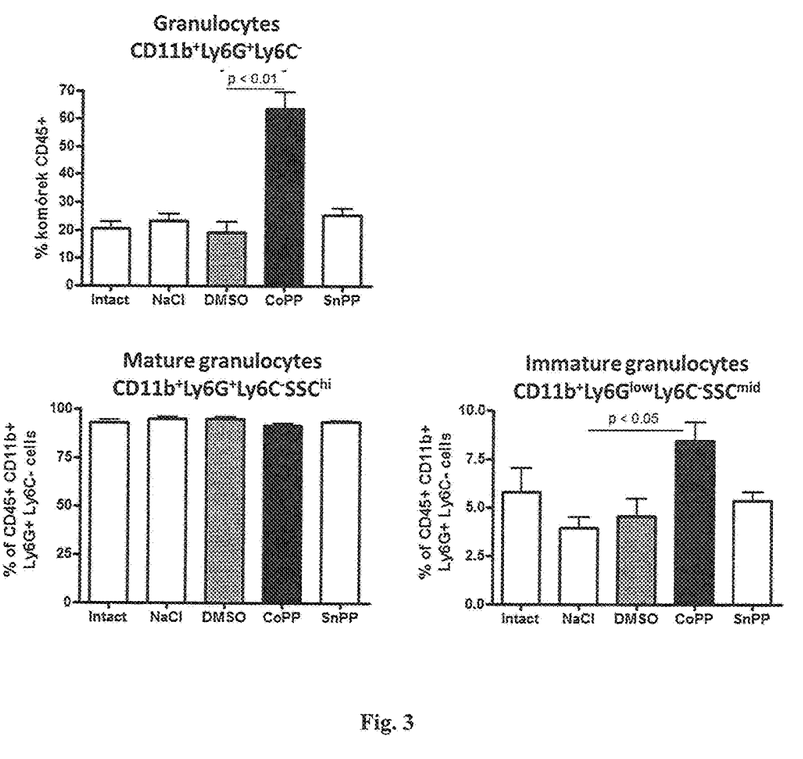
FIG. 3—the percentage of granulocytes in peripheral blood in C3H mice after administration of the test compounds; (test ANOVA+Bonferroni test), FIG. 4—the percentage of granulocytes in the peripheral blood of C57BL6xFVB mice after administration of CoPP; (test ANOVA+Bonferroni test), FIG. 5—concentration of cytokines and growth factors in plasma of C3H mice after administration of test compounds; (test ANOVA+Bonferroni test), FIG. 6—concentration of cytokines and growth factors in plasma of C57BL6xFVB mice after administration of CoPP; (test ANOVA+Bonferroni test), FIG. 7—singlet oxygen generation quantum yield ($\Phi_\Delta$) for CoPP and SnPP in reference to phenalenone, measured by flash photolysis.
Figure 4:
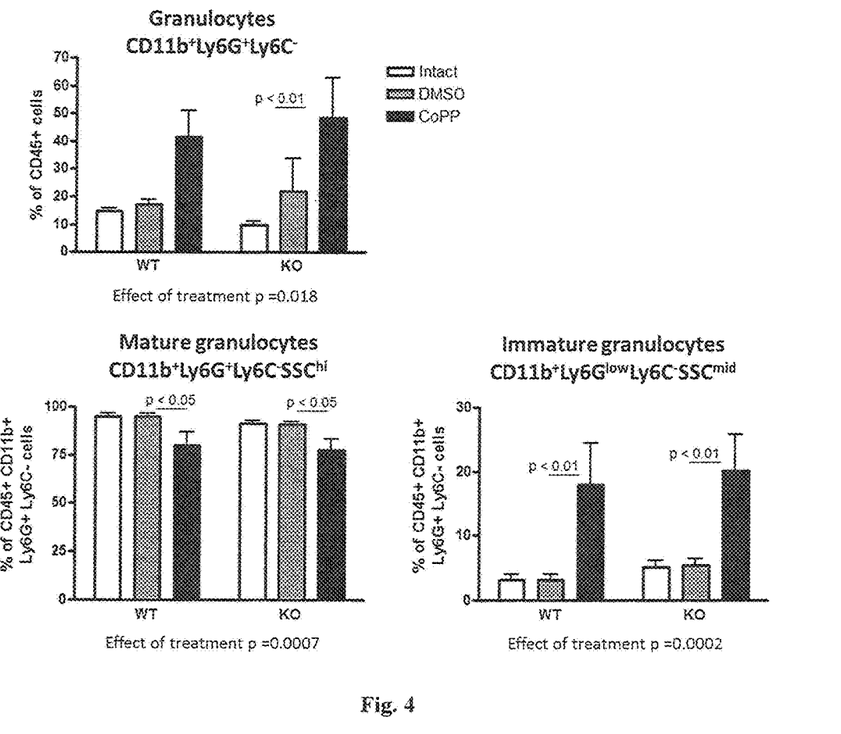

CoPP is used in scientific experiments, both in vitro and in vivo as heme oxygenase-1 inducer. However, the inventors have demonstrated using knockout mice HO-1 (HO-1 KO) that the mobilization of cells from bone marrow using CoPP does not depend on the activity of HO-1 (FIG. 4). In HO-1 KO mice CoPP works in a similar manner as in wild type mice. In some of the experiments tin protoporphyrin IX (SnPP), which is an inhibitor of the enzymatic activity of HO-1, was also used. Use of SnPP did not affect the majority of the measured parameters, what supports the independence of the observed effects of the action of HO-1 (FIG. 1,3,5).

The invention has been described in the examples.

Example 1

CoPP was administered to mice intraperitoneally at a dose of 10 mg/kg of body weight, three times at intervals of two days. Control mice received only the solvent (DMSO). In one experiment tin protoporphyrin (SnPP) was also used.

Figure 2:
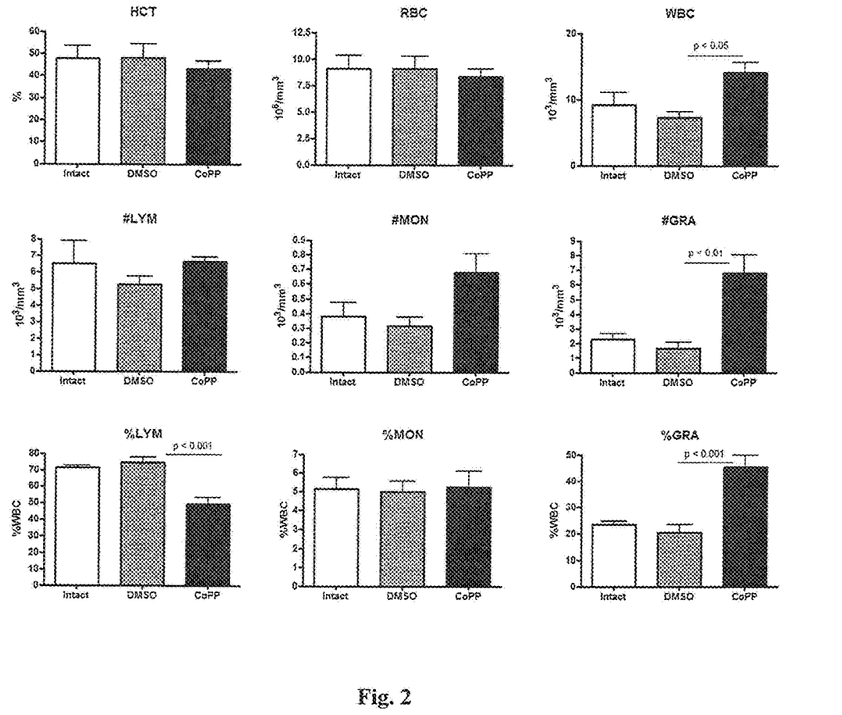
FIG. 2—peripheral blood cell counts in C57BL6xFVB strain after administration of CoPP; (test ANOVA+Bonferroni test)

The day after the last administration of CoPP the mice were sacrificed and samples were collected for analysis. Complete blood counts were obtained using a hematology analyzer. In addition, the phenotype and the quantity of leukocytes in the peripheral blood, bone marrow and spleen was analyzed in more detail using a flow cytometer. Moreover, concentrations of 32 cytokines and growth factors in plasma were analyzed. The results of analyzes indicate that mice that were treated with CoPP had increased number of white blood cells (WBC) in the blood compared to mice that received only DMSO (3-fold in C3H mice, 2-fold in C57BL6xFVB mice). In both strains, there was a significant increase in the number of granulocytes (6.7-fold in C3H mice, 4-fold in C57BL6xFVB mice). There were no changes in the parameters such as hematocrit (HCT) and the number of erythrocytes (RBC) (FIG. 1, FIG. 2)

Example 2

The populations of leukocytes, in which the size of affected administration of CoPP, was characterized in more detail using a flow cytometer. It has been shown that the administration of CoPP resulted in the increase in the number of immature granulocytes (CD11b$^+$/Ly6G$^{low}$/Ly6C$^-$/SCC$^{mid}$ phenotype) (FIG. 3, FIG. 4).

Example 3

Figure 5:
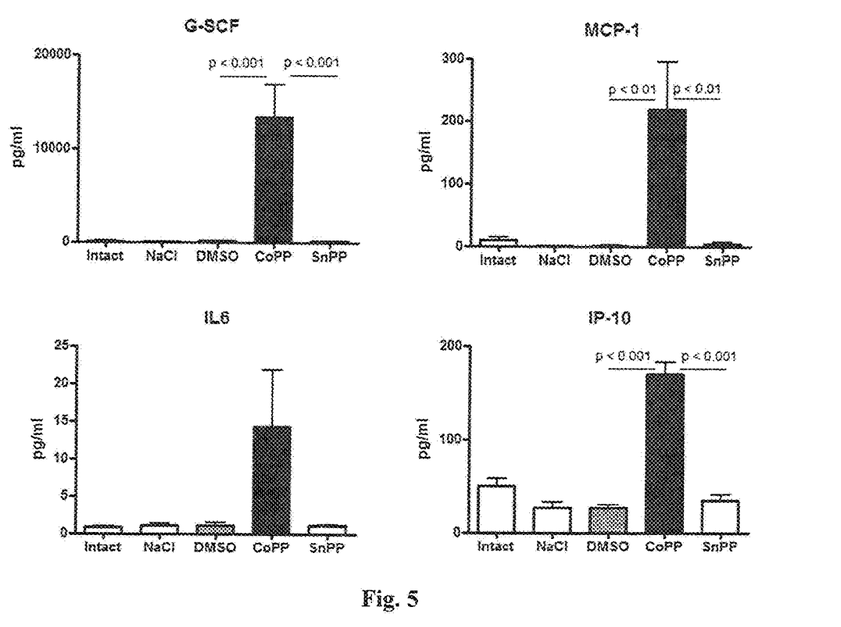
Figure 6:
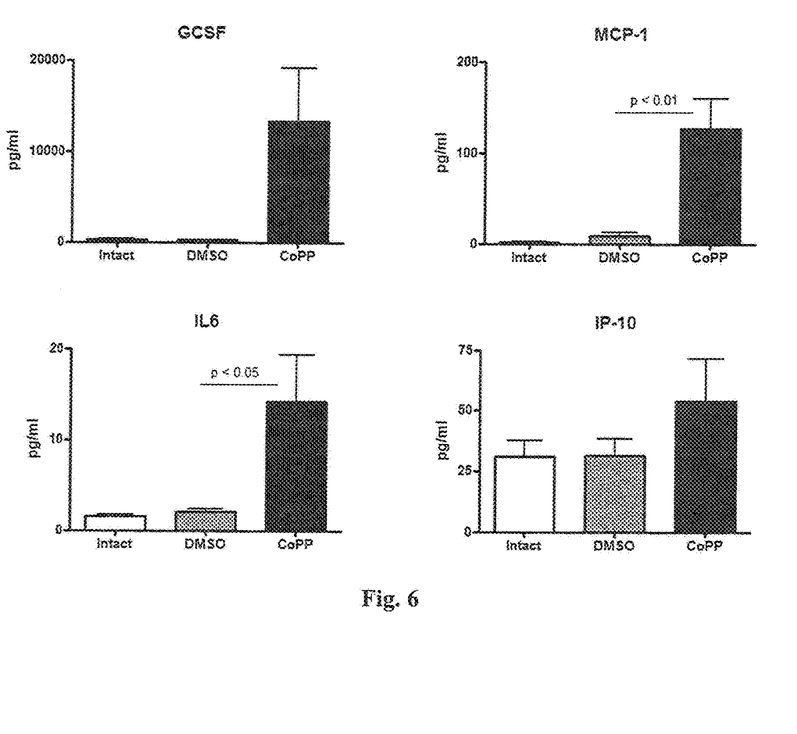

In order to investigate the mechanism responsible for the increase of the leukocytes (especially granulocytes) number, after administration of CoPP, the concentrations of cytokines and growth factors in the plasma were measured using the Luminex system. An increase in levels of granulocyte colony stimulating factor (G-CSF), chemokines MCP-1 (CCL2) and IP-10 (CXCL-10) and interleukin 6 was observed (FIG. 5, FIG. 6).

Example 4

Figure 8:
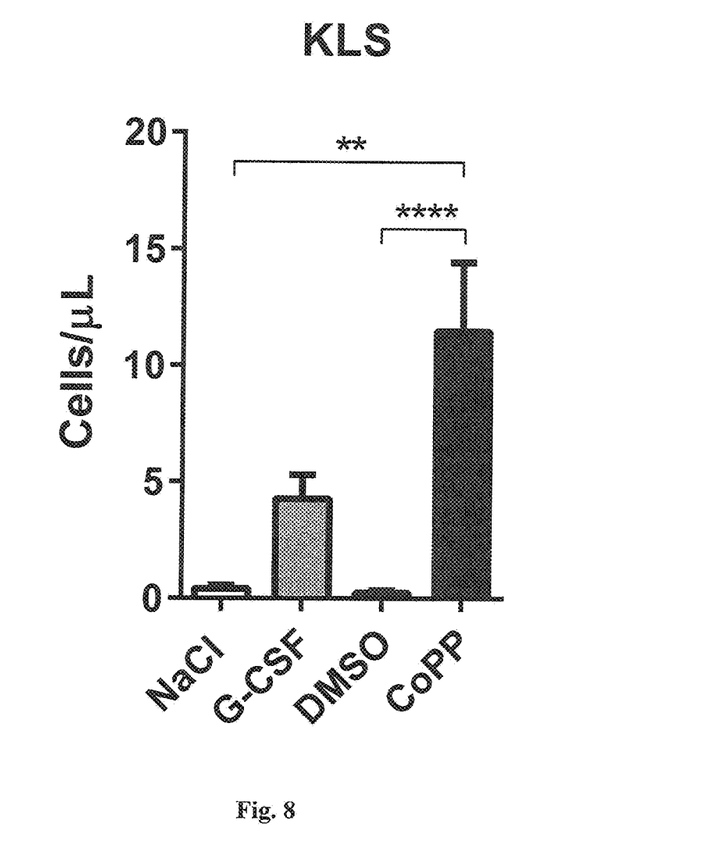
FIG. 8—HSPC numbers in the blood of C57BL6xFVB mice treated with G-CSF and CoPP.

Effects of CoPP and exogenous G-CSF were compared. Mice were iterated with CoPP at the dose of 10 mg/kg (15 μmol/kg). Recombinant human G-CSF (rhG-CSF, Amgen) was used at the dose of 250 μg/kg. Compounds were injected i.p. daily for five days. Administration od CoPP mobilized higher number of HSPC (hematopoietic stem/progenitor cells) than administration of exogenous G-CSF (FIG. 8).

What is claimed is:

1. A method for the treatment of at least one disease selected from the group consisting of congenital neutropenia, neutropenia caused by chemotherapy, radiotherapy and pharmacologically-induced neutropenia, acute myeloid leukemia, acute lymphocytic leukemia, and myelodysplastic syndromes, the method comprising:
   inducing mobilization of bone marrow cells to peripheral blood by administering to a patient in need of an increase of G-CSF in the patient's bone marrow or peripheral blood, an effective amount of a solution containing cobalt protoporphyrin IX by intramuscular or subcutaneous injection or oral administration, to increase the available G-CSF in the bone marrow or peripheral blood.

2. The method according to claim 1, wherein the cobalt protoporphyrin IX is used in a dose range of 0.5-50 μmol/kg of body weight.

3. A method for increasing the amount of circulating hematopoietic stem cells in peripheral blood for subsequent isolation in a process of apheresis for allogeneic or autologous transplantation, the method comprising:
   inducing mobilization of bone marrow cells to peripheral blood by administering to a patient in need of an increase in G-CSF in the patient's bone marrow or peripheral blood, an effective amount of a solution containing cobalt protoporphyrin IX by intramuscular or subcutaneous injection or oral administration, to increase the available G-CSF in the bone marrow or peripheral blood.

4. The method according to claim 3, wherein the cobalt protoporphyrin IX is used in a dose range of 0.5-50 μmol/kg of body weight.

5. A method for the treatment of at least one disease selected from the group consisting of autoimmune diseases, systemic lupus erythematosus, inflammatory bowel diseases, rheumatoid arthritis, and diabetes in which increase in G-CSF concentration in blood is needed, the method comprising:
   inducing modulation of T cell response by G-CSF by administering to a patient in need of an increase in G-CSF in the patient's peripheral blood an effective amount of a solution containing cobalt protoporphyrin IX by intramuscular or subcutaneous injection or oral administration to increase the available G-CSF in the peripheral blood.

6. The method according to claim 5, wherein the step of inducing modulation of T cell response by G-CSF includes inducing a Th2 response.

7. The method according to claim 5, wherein the cobalt protoporphyrin IX is used in a dose range of 0.5-50 μmol/kg of body weight.

* * * * *